United States Patent
Igarashi et al.

(10) Patent No.: US 9,247,865 B2
(45) Date of Patent: Feb. 2, 2016

(54) THREE-DIMENSIONAL-IMAGE FORMING DEVICE, THREE DIMENSIONAL-IMAGE FORMING METHOD AND PROGRAM

(75) Inventors: Tatsuo Igarashi, Chiba (JP); Satoki Zenbutsu, Chiba (JP)

(73) Assignee: NATIONAL UNIVERSITY CORPORATION CHIBA UNIVERSITY, Chiba-Shi, Chiba (JP)

( * ) Notice: Subject to any disclaimer, the term of this patent is extended or adjusted under 35 U.S.C. 154(b) by 1414 days.

(21) Appl. No.: 12/302,480

(22) PCT Filed: May 31, 2007

(86) PCT No.: PCT/JP2007/061100
§ 371 (c)(1),
(2), (4) Date: Nov. 25, 2008

(87) PCT Pub. No.: WO2007/139187
PCT Pub. Date: Dec. 6, 2007

(65) Prior Publication Data
US 2009/0207241 A1 Aug. 20, 2009

(30) Foreign Application Priority Data
May 31, 2006 (JP) .................................. 2006-151936

(51) Int. Cl.
*H04N 13/00* (2006.01)
*A61B 1/04* (2006.01)
(Continued)

(52) U.S. Cl.
CPC ............... *A61B 1/042* (2013.01); *G06T 7/0053* (2013.01); *G06T 7/0065* (2013.01); *G06T 17/00* (2013.01);
(Continued)

(58) Field of Classification Search
CPC .................................................. G02B 23/2415
USPC .................................... 348/45, 48, 68, 84, 85
See application file for complete search history.

(56) References Cited

U.S. PATENT DOCUMENTS 5,162,907 A * 11/1992 Keating et al. ........... 375/240.16
5,173,865 A * 12/1992 Koike et al. .................... 702/155
(Continued)

FOREIGN PATENT DOCUMENTS

JP 5-21988 A 1/1993
JP 5-340721 A 12/1993
(Continued)

OTHER PUBLICATIONS

Sakai et al., "Adaptive Displaying Deformable Dissection Image of Intestine by Changing Point of Interest" Information Processing Society of Japan Kenku Hokoku, 2006, vol. 2006, No. 51, pp. 167-172.
(Continued)

*Primary Examiner* — Joon H Hwang
*Assistant Examiner* — Sherman Lin
(74) *Attorney, Agent, or Firm* — Buchanan Ingersoll & Rooney PC

(57) ABSTRACT

In a three-dimensional image forming device for forming a phantom three-dimensional image in accordance with an image of an inner face of a tubular structure to be observed, luminance information of pixels corresponding to a prescribed range of each frame image of the tubular structure is obtained under prescribed lighting conditions when an imaging device with an optical axis extending to an axial direction of the tubular structure moves, a relative distances in a depth direction between points and an objective lens is calculated in accordance with the luminance information, pixels corresponding to the prescribed range of each frame image in the inner face of the tubular structure is arrayed in reflection of the relative distance, and the arrayed pixels are combined for a plurality of the frame images to form a three-dimensional image of the inner face of the tubular structure.

14 Claims, 17 Drawing Sheets

(51) Int. Cl.
*G06T 7/00* (2006.01)
*G06T 17/00* (2006.01)
*A61B 5/107* (2006.01)

(52) U.S. Cl.
CPC ..... *A61B 5/1076* (2013.01); *G06T 2207/10016* (2013.01); *G06T 2207/10068* (2013.01); *G06T 2207/30028* (2013.01)

(56) References Cited

U.S. PATENT DOCUMENTS

| | | | |
|---|---|---|---|
| 5,469,254 A * | 11/1995 | Konomura | 356/241.1 |
| 2002/0148947 A1 * | 10/2002 | Kakiuchi et al. | 250/208.1 |
| 2005/0259888 A1 * | 11/2005 | Ozluturk | 382/260 |
| 2006/0045377 A1 * | 3/2006 | Kawai | 382/274 |

FOREIGN PATENT DOCUMENTS

| | | |
|---|---|---|
| JP | 06-042300 | 2/1994 |
| JP | 11-66316 A | 3/1999 |
| JP | 11-337845 A | 12/1999 |
| JP | 2000-19424 A | 1/2000 |
| JP | 2000-121339 A | 4/2000 |
| JP | 2000-331168 A | 11/2000 |
| JP | 2001-224594 A | 8/2001 |
| JP | 2002-191554 A | 7/2002 |
| JP | 2003-32674 A | 1/2003 |
| JP | 2003-535659 A | 12/2003 |
| JP | 2006-187551 A | 7/2006 |
| WO | WO 2004/096008 A2 | 11/2004 |

OTHER PUBLICATIONS

Supplemental European Search Report dated Jul. 6, 2010, issued in the corresponding European Application No. 07744488.3-2319 (PCT/JP2007061100).
PCT/ISA/210.
PCT/ISA/237.

* cited by examiner

Fig.2
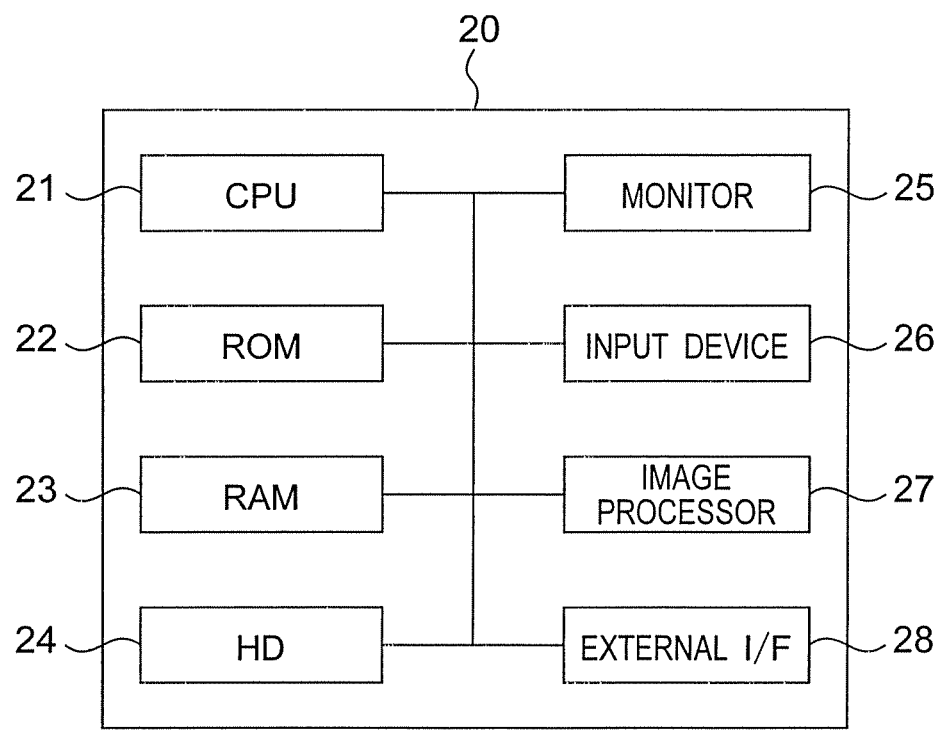
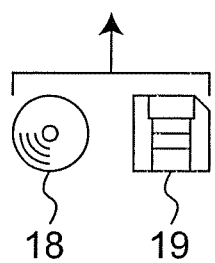

TIME

TIME

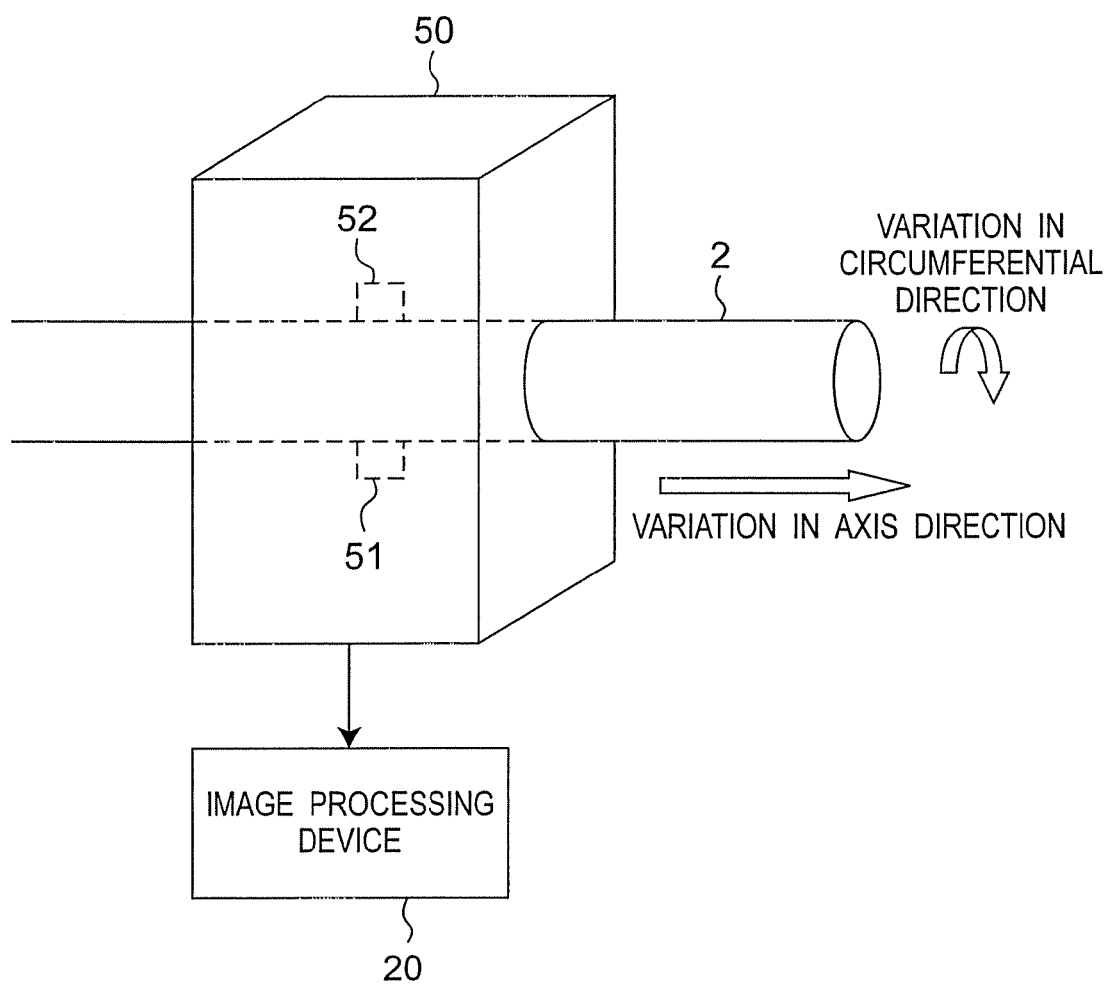

THREE-DIMENSIONAL-IMAGE FORMING DEVICE, THREE DIMENSIONAL-IMAGE FORMING METHOD AND PROGRAM

TECHNICAL FIELD

The present invention relates to a three-dimensional image forming device for forming continuous three-dimensional images at high speed, on the basis of a relative distance between an objective lens and points inside a tubular structure, in which the relative distance is calculated from continuous images or video images inside the tubular structure captured by a camera or an endoscope disposed or inserted in a tubular structure such as tunnel, sewerage pipe, digestive tract or tubular organ of a patient, or the like.

BACKGROUND ART

Conventionally, regarding use of an endoscope device, generally, the observation region depending on the viewing field of the endoscope inserted in a tubular structure is observed grossly or displayed on a video camera, and is recorded as still image or vide image in a recoding range specified by an observer. In this case, the observed or displayed range is limited within the observation viewing field of the endoscope, and the entire picture is recorded by repeating record of image in local range. In this method, the entire picture cannot be displayed as one seamless picture, and it lacks objectivity in identification of the position of the region of interest. Other method of continuously recording the entire image includes a video imaging method, but the entire picture cannot be displayed simultaneously, and it takes time in viewing. In the conventional methods, only two-dimensional images are recorded, and a three-dimensional structure cannot be recognized. Further, in the conventional methods, it is difficult to record objectively the hardness or motion of tissues composing a tubular structure.

For example, patent document 1 discloses an image forming system for forming continuous seamless expanded still image data inside a tubular structure of this type. This image forming system includes means for acquiring digital image data, pipe projection converting means for forming an expanded diagram in circumferential direction inside the tubular structure for each frame of the acquired digital image data, means for mosaicing, means for compressing image data, and means for compressing image data. The image forming system constructs an entire image by linking in the direction of the central axis of the tubular structure expanded diagrams in circumferential direction of each frame of the endoscopic video image.

Patent document 2 discloses a method of creating an entire image by taking images inside of a tubular structure while monitoring the posture and position information of a camera moving in the tubular structure and linking a plurality of images while matching the observation field of the camera.

Patent document 3 discloses a method of measuring the shape of the inside of a body stereoscopically by directional lighting using an endoscope with a directional scanning lighting device provided at the leading edge of the endoscope. Patent document 4 discloses a method of calculating the three-dimensional information of the subject based on interference fringes formed on the subject and distance information, using an endoscope with an interference fringe projecting unit and a laser spot projecting unit for measuring the distance provided at the leading edge of the endoscope.

Patent document 5, for example, discloses a method of detecting three-dimensional information of the subject by taking images at arbitrary time intervals while varying the amplitude of the illuminating light, and measuring the distance of each point based on the luminance of each point of the taken image and the degree of change of image gain.

Patent document 6, for example, discloses a method of creating strip-like images from 360-degree spatial video image captured using a camera moving in the tubular closure through convex mirror or fisheye lens installed in front of the camera and linking them while correcting them in the direction of camera's motion to display one entire image.

Patent document 7, for example, discloses a method of calculating the length or area of the subject by calculating the relative positions between a pipe having a single cross section and an endoscope from the endoscopic images inside the pipe observed by the endoscope moving in the pipe.

Patent document 8, for example, discloses image processing means for forming a three-dimensional model from a plurality of two-dimensional images taken while varying the optical parameters. Patent document 9 discloses a technique of forming a three-dimensional model from a plurality of images taken while changing the optical parameters. Patent document 10 discloses a technique of extracting stereoscopic information by parallax, by separating the subject observed by an endoscope with a color filter into color components.

Patent document 11, for example, discloses a technique of measuring the hardness of biological tissues by calculating reflection signals from the biological tissues with modulated ultrasonic waves emitted from an ultrasonic transducer mounted at the leading edge of an endoscope.

PATENT DOCUMENT

Patent document 1: JP-A-2003-32674
Patent document 2: JP-A-11-66316
Patent document 3: JP-A-2003-535659
Patent document 4: JP-A-05-21988
Patent document 5: JP-A-2000-121339
Patent document 6: JP-A-2000-331168
Patent document 7: JP-A-05-340721
Patent document 8: JP-A-11-337845
Patent document 9: JP-A-2002-191554
Patent document 10: JP-A-2000-19424
Patent document 11: JP-A-2001-224594

DISCLOSURE OF INVENTION

In the techniques disclosed in patent documents 1 and 6, expanded images are created from the images taken by one camera, and it is required to extract the central axis of the tubular structure from images. Thus the images cannot be linked under the situation in which the endoscope moves in an irregular-shaped tubular structure, that is, the situation in which the relative positions of the optical axis of the camera and the central axis of the tubular structure are always varying largely.

In the technique shown in patent document 2, since the posture and position of the camera are always measured, and the measuring device and information processing device for the measurement are needed, and the adjustment and calculation are complicated. In the techniques shown in patent documents 3, 4 and 9, a plurality of devices must be additionally installed to the endoscope main body.

In the technique shown in patent document 5, the distance to the camera is calculated from the degree of change of luminance of reflected light from the subject taken at an arbitrary time interval with the light varying in amplitude, and a sensor of excellent resolution or expensive device is needed.

Further it is impossible to measure when the subject is very close to the camera, or the subject moves rapidly or deforms repeatedly. In the technique shown in patent document 8, a three-dimensional model is created from a plurality of images taken with the optical parameters being changed, and it is not applicable to the subject moving very fast, and an optical device is additionally required. The technique shown in patent document 7 is based on the measurement of the subject inside a pipe having a single cross section, and it is not applicable to an irregular-shaped tubular structure. The technique shown in patent document 10 requires a stereoscopic endoscope and device newly, and stereoscopic information and color information must be reconstructed by parallax and arrayed properly for display of continuous stereoscopic image. Thus the calculation is complicated, and it is not applicable to images taken in a fast motion. The technique shown in patent document 11 requires an ultrasonic device to be attached to the leading edge of an endoscope. Further air must not be present between the ultrasonic device and the biological tissues, and thus a new device and a complicated arithmetic operation should be required, and the application in the medical field is limited.

The present invention is devised in the light of the technical problems above stated, and it is hence an object thereof to present a three-dimensional image forming device, method and program capable of forming easily a three-dimensional image of a tubular structure even in a situation where the relative position between the central axis of an irregular-shaped and moving tubular structure and the optical axis of the imaging means is varied.

A first aspect of the invention relates to a three-dimensional image forming device for forming a three-dimensional image on the basis of images of the inner face of a tubular structure to be observed.

The three-dimensional image forming device includes an imaging unit having an optical axis extending in the axial direction of the tubular structure, for obtaining a plurality of frame images while moving in the tubular structure under specified lighting condition;

a luminance information extracting unit for extracting luminance information of pixels corresponding to a specified range of each frame image of the inner face of the tubular structure acquired by the imaging unit;

a distance information calculating unit for calculating relative distances in the depth direction between points on the inner face of the tubular structure and an objective lens (imaging unit) on the basis of the luminance information extracted by the luminance information extracting unit; and a three-dimensional image forming unit for forming a three-dimensional image of the inner face of the tubular structure by arraying the pixels corresponding to the specified range of each frame image of the inner face of the tubular structure while reflecting the relative distances to the arraying, and combining the arrayed data for a plurality of frame images.

In a second aspect of the invention, the three-dimensional image forming device further includes a change amount detecting device for measuring change amount of imaging unit (for example, an endoscope) in the circumferential direction and axial direction. The three-dimensional image forming unit constructs a three-dimensional image of the inside of the tubular structure by combining the images corresponding to the specified range of each frame image on the inner face of the tubular structure by data arrays for the portion of a plurality of frame images while reflecting the motion information (detected information) in the circumferential direction and axial direction at the leading edge of the imaging unit measured by the change amount detecting unit.

The three-dimensional image forming device may further include test line setting means for setting on each frame image a circular test line having a center corresponding to the optical axis of the imaging unit, as the specified range of the frame image from which luminance information is extracted by the luminance information extracting unit. In this case, the luminance information extracting unit extracts the luminance information of pixels located on the test line in each frame image.

The three-dimensional image forming device may further include a color information extracting unit for extracting color information of pixels composing each frame image of the inner face of the tubular structure obtained by the imaging unit, and a color information adding unit for adding the color information extracted by the color information extracting unit to each pixel composing the three-dimensional image constructed by the three-dimensional image forming unit.

The luminance information may be luminance information about red, green, blue, or the mixed color thereof for composing each frame image. In addition, the imaging means may be an endoscope.

According to the invention, in a state of fluctuation of relative positions between the central axis of an irregular-shaped and moving tubular structure and the optical axis of the imaging means, a three-dimensional image of the tubular structure can be easily formed at high speed. By forming a three-dimensional image at high speed, at the time of endoscopic diagnosis, in addition to conventional diagnosis based on the shape data and color data, the motion of the tubular structure can be accurately examined and recorded. Further, by forming a three-dimensional image at high speed while injecting an appropriate gas or liquid into the inner space of the tubular organ, at the time of endoscopic diagnosis, the information of hardness or tension of the biological tissues composing the tubular organ can be recorded.

Conventionally, a lot of images must be taken to record an endoscopic image, but according to the invention, a three-dimensional image including the entire observation range can be formed, and thus the user can easily recognize the position or shape of a diseased portion, and the diagnostic precision of endoscopic examination is enhanced. In addition, the memory capacity for storing images can be reduced, and the image reviewing time can be shortened.

Further, since the color information is added to each pixel for forming the three-dimensional image, the three-dimensional image similar to the actual subject image can be formed. The features of the observation object can be more easily recognized.

A three-dimensional image similar to the actual observation object, by selectively using luminance information of red, green, blue, or mixed color thereof depending on the hue of the observation object. For example, when observing digestive tract or tubular organ of a patient, the luminance information relating to a hue similar to the complementary color of the hue of the observation object, for example, green color is used, so that a three-dimensional image similar to the actual subject can be formed.

BRIEF DESCRIPTION OF DRAWINGS

FIG. 2 is a block diagram of basic configuration of an information processing device for providing the three-dimensional image forming device.

FIG. 15 is a diagram of motion detecting device of three-dimensional image forming device in Embodiment 2.

Figure 1:
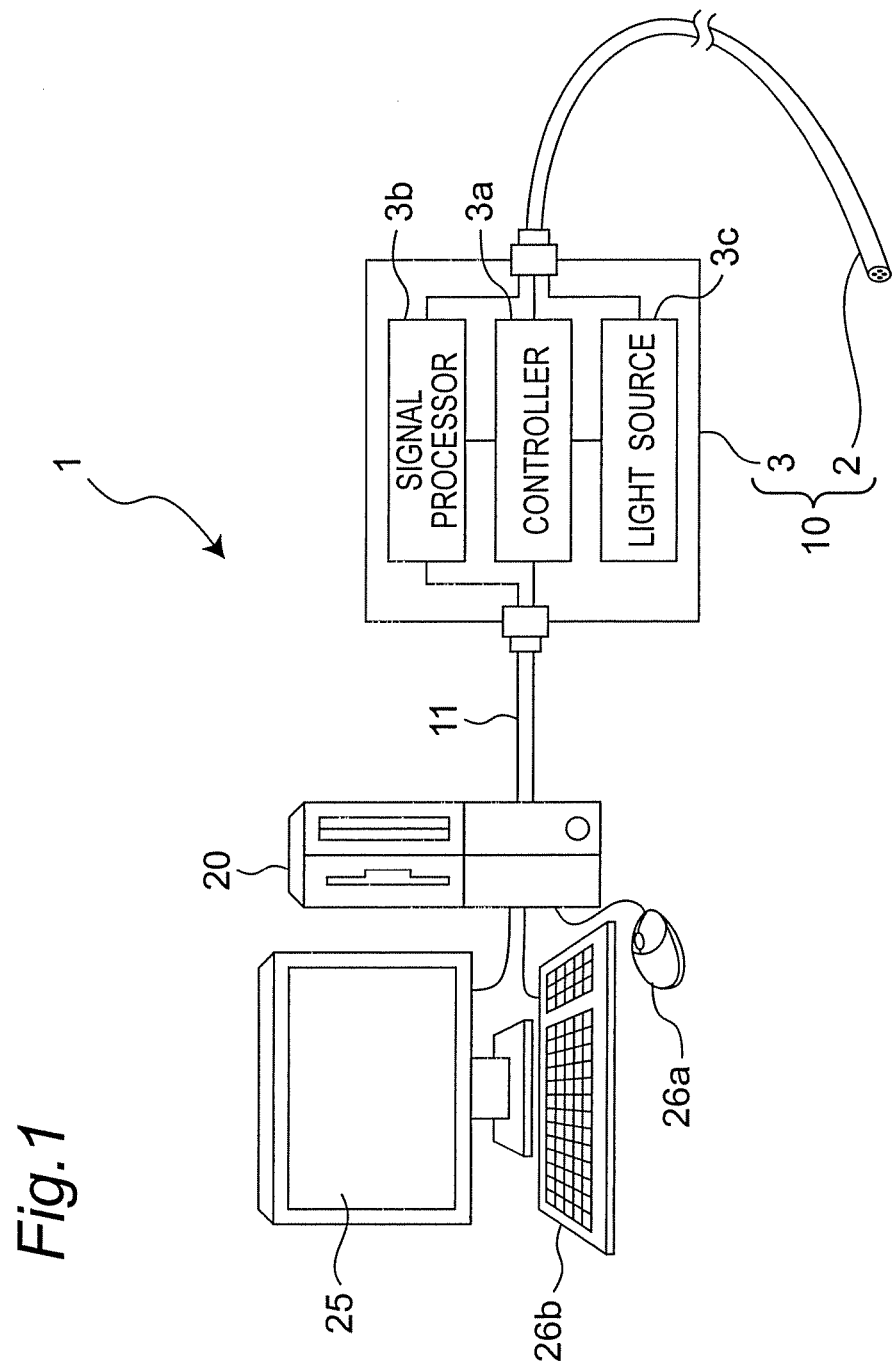
FIG. 1 is a block diagram of entire configuration of a three-dimensional image forming device in an embodiment of the invention.

DESCRIPTION OF THE REFERENCE SINGS 1 three-dimensional image forming device
2 endoscope
2a objective lens
2b lighting fiber
3 control unit
10 endoscopic device
18 optical disk
19 floppy disk
20 information processing device
22 ROM
23 RAM
24 hard disk
25 monitor
27 image processor
30 tubular body
30a inner face of tubular body
50 motion detecting device
51 circumferential direction sensor
51 axial direction sensor
F optical axis of objective lens
S1, S2 observation region

BEST MODE FOR CARRYING OUT THE INVENTION

Embodiments of the invention are described below with reference to the accompanying drawings.

Embodiment 1

FIG. 1 is a block diagram of entire configuration of a three-dimensional image forming device in embodiment 1 of the invention. The three-dimensional image forming device 1 includes an endoscopic device 10 for taking images of inside face of tubular organ, and obtaining a video file composed of a plurality of frame images, and an information processing device 20 composed of general-purpose personal computer or the like and connected to the endoscopic device 10, for outputting display signal of the video file acquired by the endoscopic device 10 and executing a process of forming an artificial three-dimensional image based on the frame images extracted from the video file. The endoscopic device 10 and the information processing device 20 are connected by way of a cable 11 such as USB cable. The data can be transmitted between the two devices, for example, the video file acquired by the endoscopic device 10 is transmitted to the information processing device 20, or a command signal is transmitted from the information processing device 20 to the endoscopic device 10. A video capture board may be interposed between the endoscopic device 10 and the information processing device 20.

The endoscopic device 10 has an endoscope 2 inserted in, for example, a tubular organ, for taking images of hollow inside, and a control unit 3 for compiling a video file on the basis of signals entered through the endoscope 2. The configuration of the endoscope 2 is explained later with reference to FIG. 3. The control unit 3 has a controller 3a for controlling the components in the unit 3, a signal processor 3b for compiling a video file of inside image of hollow based on signals entered through the endoscope 2, and a light source 3c as light source for illumination light which is emitted from the leading edge of the endoscope 2 to the observation object. The controller 3a controls imaging operation of the endoscope 2 and on/off operation of lighting, or adjusts the quantity of light supplied to the endoscope 2 from the light source 3c, according to the user's operation.

The configuration of the three-dimensional image forming device 1 is not particularly specified, and, for example, instead of the endoscopic device 10 for observing the inside of tubular organ, an endoscopic device and a video camera system for observing the inner face of tunnel or sewerage may be used. As the information processing device 20, instead of the stationary (desktop) personal computer, a laptop personal computer may be used.

FIG. 2 is a block diagram of basic configuration of the information processing device 20. The information processing device 20 includes a CPU 21 for executing sequence control of components in the information processing device 20 according to program such as operating system (OS) as basic software, a ROM 22 for storing a boot program to be executed upon start-up of the information processing device 20, a RAM 23 used for buffer area as working area necessary for execution of a program, a hard disk drive (HD in the diagram) 24 for storing OS, application program, and various data, a monitor 25 which is a display device for displaying various information such as application screen, an input device 26 such as mouse 26a or keyboard 26b, an image processor 27 for forming a three-dimensional image by operating various processes on the basis of the video file input from the endoscopic device 10, and an external interface (external I/F in the diagram) 28 for sending/receiving data to\from an external device. Although not shown, the information processing device 20 may also have an optical disk drive, floppy (registered trademark) disk drive, and others.

In the embodiment, a three-dimensional image forming program is stored in the ROM 22 (or hard disk 24). Reading out this program and executing it, the image processor 27 of the information processing device 20 achieves the following functions. A plurality of frame images are extracted sequentially from the video file input from the endoscopic device 10. Pixel data are acquired from each frame image and arrayed. The arrayed pixel data from the frame image for a plurality of frame images are combined so as to form a three-dimensional image. The video file input from the endoscopic device 10 may be stored in the hard disk 24 of the information processing device 20, or may be transferred to a printer (not shown) for print output for specified frame images.

Figure 3:
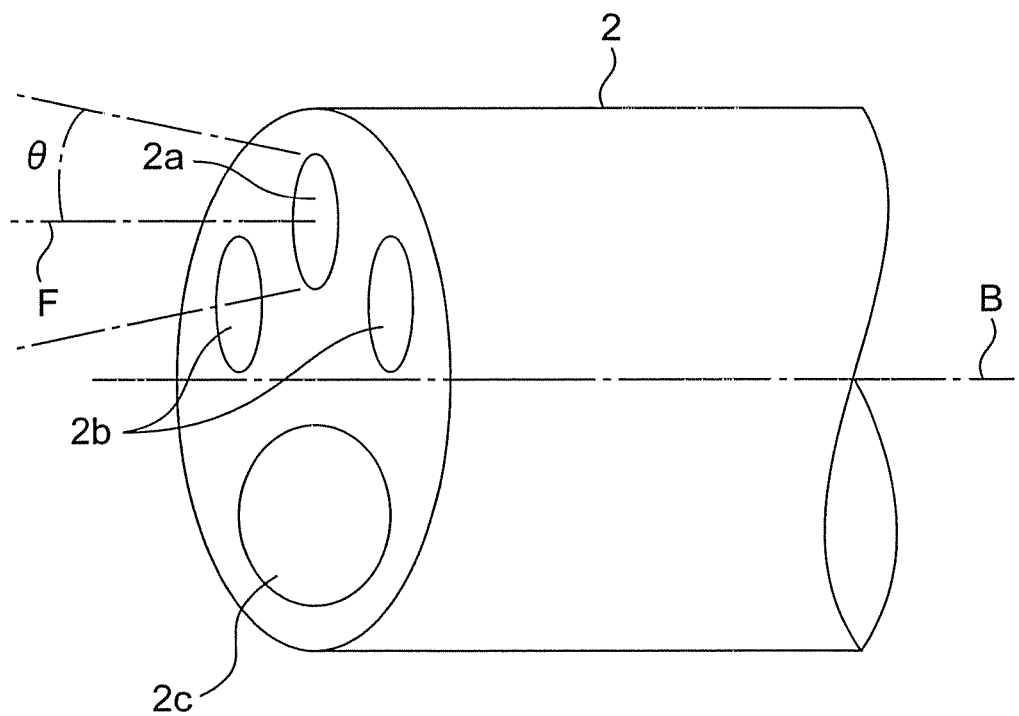
FIG. 3 is a diagram showing a configuration of a leading edge of an endoscope in the endoscopic device composing the three-dimensional image forming device.

FIG. 3 is a magnified view of the leading edge of the endoscope 2. As known from the diagram, the objective lens 2a to the observation object, a pair of optical fibers 2b for lighting, and operation channel 2c such as forceps channel or suction channel are exposed and disposed at the leading end of the endoscope 2. Such configuration is a known art, and the endoscope 2 is not particularly specified, and, for example, one or three or more optical fibers for lighting may be used. In the endoscope 2, the objective lens 2a has optical axis F extending in parallel to or at a specific angle to the central axis (indicated by B) of the endoscope 2, and has a viewing angle of θ degrees vertically and laterally to the optical axis F.

When taking images of inside of tubular organ, it is ideal to move the endoscope 2 along the central axis of the hollow. However, actually inside face of the tubular organ is irregular in shape and is moving, the posture of the endoscope 2 in the hollow varies, and hence the relative position of the central axis of the hollow and the optical axis F of the objective lens 2a is always fluctuating.

Figure 4A:
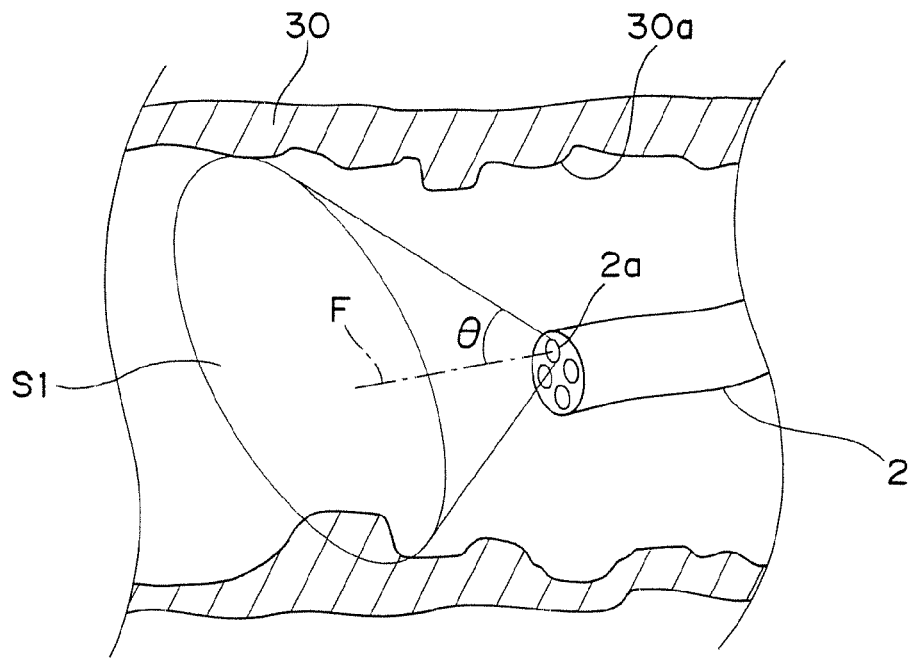
FIG. 4A is a diagram showing the observation region with an endoscope inserted and inclined downward in a tubular space.
Figure 4B:
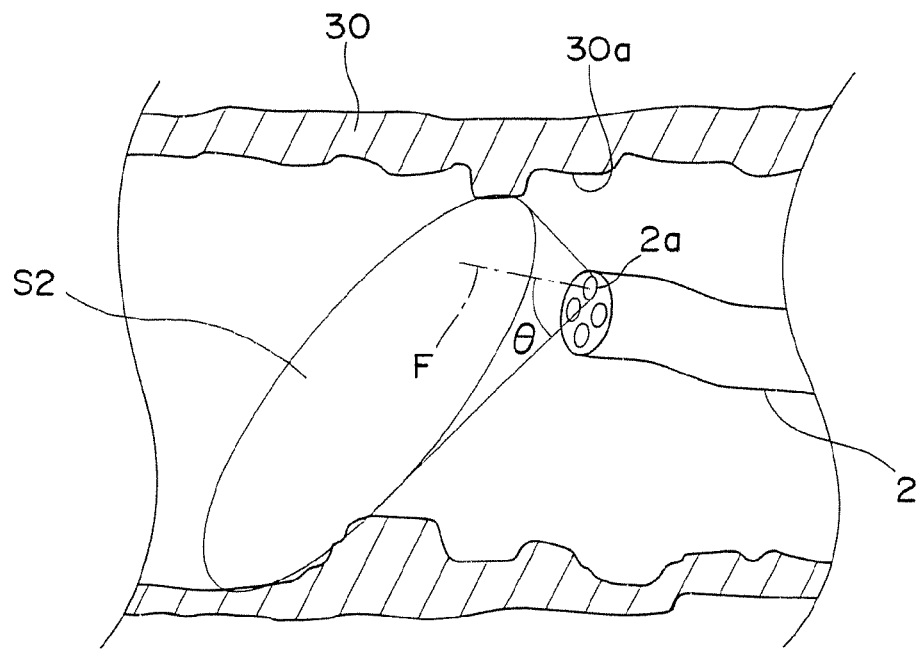
FIG. 4B is a diagram showing the observation region with an endoscope inserted and inclined downward in a tubular space.

Referring now to FIGS. 4A and 4B, the description is made to change in observation region by the objective lens 2a due to change in posture of the endoscope 2 in the tubular body 30, and relation between the distance between the objective lens 2a and the observation object and the intensity of incident light to the objective lens 2a. As shown in FIG. 4A, when the endoscope 2 inserted in the tubular body 30 is inclined downward while being positioned nearly in the center in the vertical direction of the tubular body, the optical axis F is inclined downward, so that the observation region is a region as indicated by reference sign S1. In this case, at the upper inner side of the tubular body 30, a region far from the objective lens 2a falls in the observation region S1, and at the lower inner side of the tubular body 30, a region close to the objective lens 2a falls in the observation region S1.

As shown in FIG. 4B, when the endoscope 2 inserted in the tubular body 30 is inclined upward while being positioned nearly in the center in the vertical direction of the tubular body, the optical axis F is inclined upward, so that the observation region is a region as indicated by reference sing S2. In this case, at the upper inner side of the tubular body 30, a region close to the objective lens 2a falls in the observation region S2, and at the lower inner side of the tubular body 30, a region distant from the objective lens 2a falls in the observation region S2.

Figure 12:
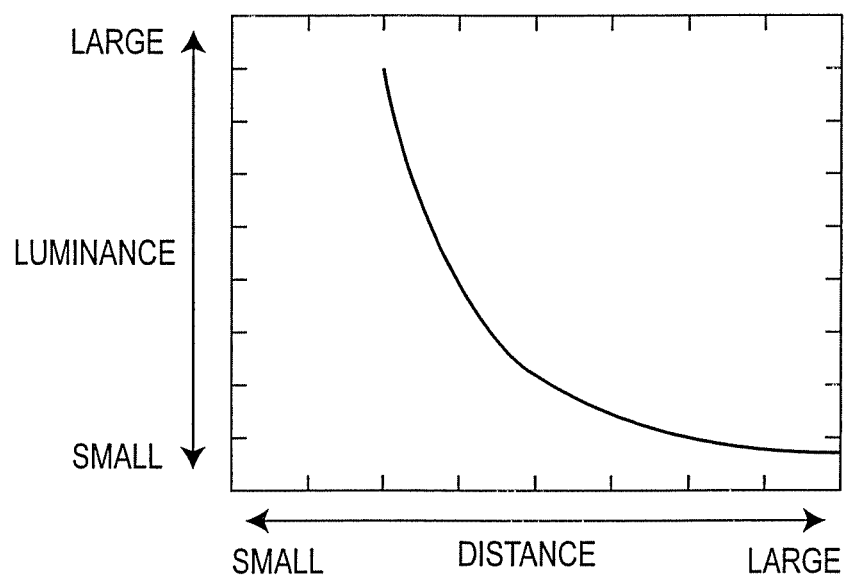
FIG. 12 is a graph showing relative changes between luminance and distance.

While taking images of inner face 30a of the tubular body, illumination light of a constant intensity is emitted to the inner face 30a from the lighting fiber 2b of the endoscope 2, and the reflected light of the illumination light from the inner face 30a enters the objective lens 2a. In this case, the luminance (intensity) of the reflected light is inversely proportional to the distance between the objective lens 2a and the inner face 30a (FIG. 12). According to that relation, the luminance of reflected light from the inner face 30a at a distant position from the objective lens 2a becomes weaker, and the luminance of reflected light from the inner face 30a close to the objective lens 2a becomes stronger. The intensity of the luminance of reflected light is reflected in the magnitude of luminance of pixels composing each frame image of the inner face 30a of tubular body acquired by conversion of the reflected light into an electrical signal by CCD (not shown) built in the endoscope 2 or the like.

Figure 5:
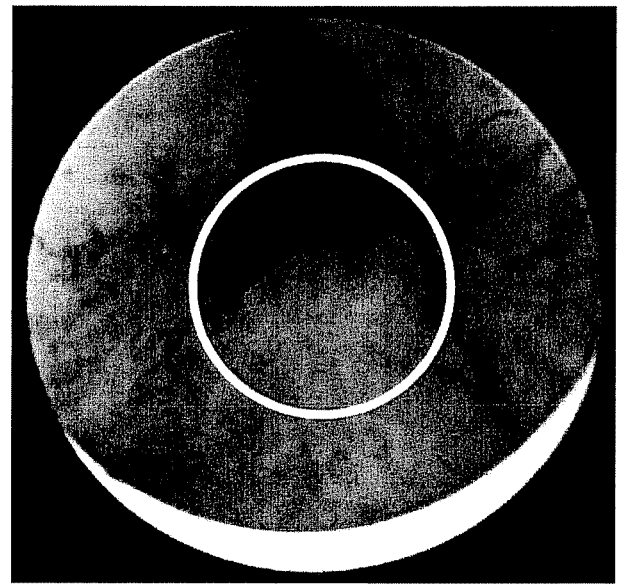
FIG. 5 is a diagram showing a frame image extracted from a video file, on which a circular test line is set as specified range from which the luminance information is extracted.

In the embodiment, the luminance information of the pixels is extracted from a specified range of each frame image of the video file which reflects intensity of reflected light from the observation object. The specified range for extracting the luminance information is set to a circular test line about the center corresponding to the optical axis F of the objective lens on each frame image. As a result, a conical depth axis connecting the lens to the test line is set. FIG. 5 shows that the test line (white circular line) as the specified range for extracting the luminance information is set on the frame image acquired by the endoscopic device 10. By setting such test line, the pixels located in the circumferential direction of the inner face 30a are extracted from each of frame images composing the video file. When the pixels for extracting the luminance information are determined, RGB values are acquired from each pixel. The luminance information is acquired based on the RGB values, and the relative distance in the depth axis direction is calculated from the luminance information. The radius of the test line may be set arbitrarily, and one test line set for acquiring a three-dimensional image of a certain observation object is commonly applied to all frame images extracted from the video file.

Figure 6:
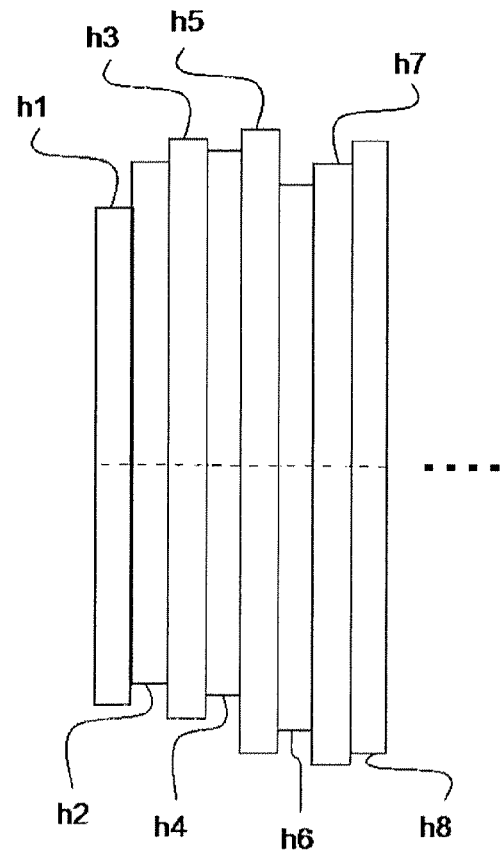
FIG. 6 is an explanatory diagram about expansion and array of pixels extracted from each frame image, and subsequent combining process.

The pixels on the test line extracted from the frame image are arrayed on a virtual space, and the arrayed pixels for a plurality of frame images are combined to construct a three-dimensional image. FIG. 6 conceptually explains that pixels located in circumferential direction of the inner face 30a of the tubular body are arrayed, and the arrayed pixels are combined for a plurality of frame images. The lateral direction in the diagram corresponds to the axial direction of the tubular body 30, and the vertical direction corresponds to the inside diameter of the tubular body 30. When combining the arrayed pixels h1 to h8, the pixels corresponding to the central axis of the objective lens 2a (pixels located at the position of 6 o'clock of the test line) are set as reference pixel, and the arrayed pixels are positioned and combined so that the reference pixels may be matched.

In the embodiment, when arraying the pixels, the width in the vertical direction is varied depending on the luminance of each pixel on the test line. For example, each pixel is plotted so that the width may be smaller as the luminance of the pixel is higher and the width may be larger as the luminance is lower. As a result, the information on inside diameter of the tubular body 30 is added.

In FIG. 6, to simplify the explanation about combination of arrayed pixels, the pixels are disposed on the same plane, but actually the pixels are expanded and arrayed so that the luminance information extracted from each pixel may reflect in a direction (depth direction) perpendicular to the sheet of FIG. 6. Hence the image is constructed three-dimensionally.

Figure 7:
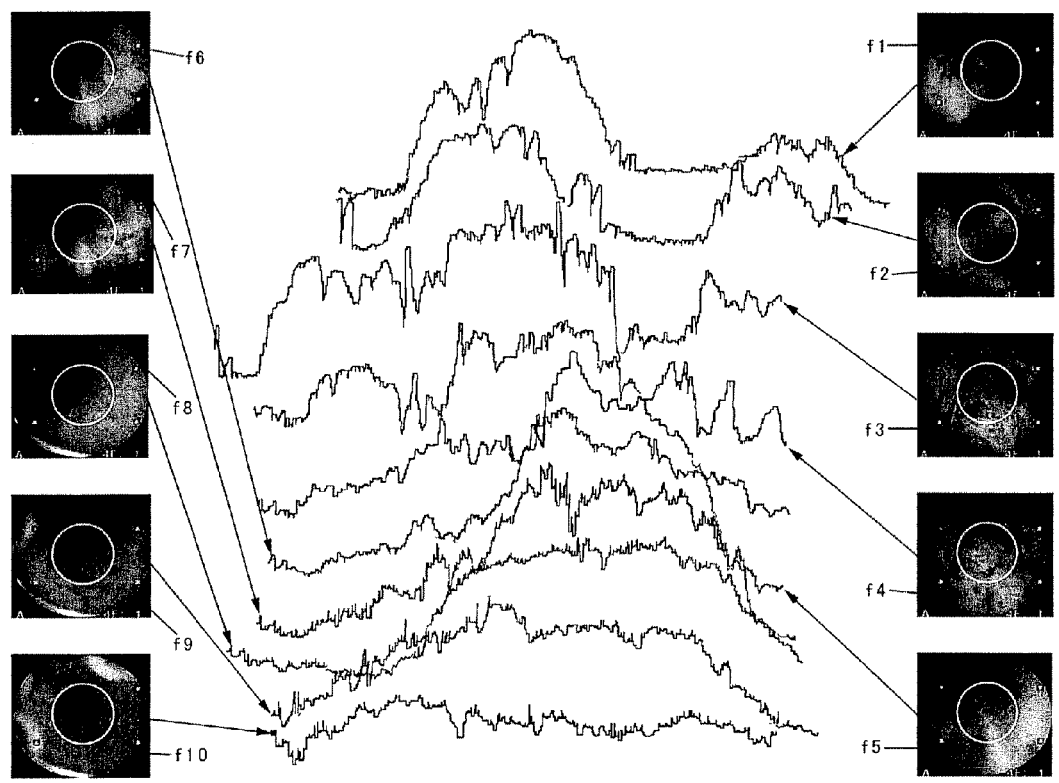
FIG. 7 is a diagram showing changes in luminance information of pixels extracted from the test line set on each frame image.

FIG. 7 is a diagram of graphs showing changes in luminance information of pixels extracted from a plurality of frame images. Herein, changes in luminance information of pixels extracted from ten frame images f1 to f10 are shifted and arranged in the sequence of extraction of the frame images. In the diagram, the lateral direction corresponds to the inside diameter of the tubular body 30, and the vertical direction corresponds to the axial direction of the tubular body 30. In FIG. 7, the change in luminance information actually to be shown in a direction perpendicular to the sheet of the diagram (depth direction) is expressed in the vertical direction in the diagram.

Figure 8:
FIG. 8 is a diagram of expanded image of inside of tubular space constructed by a conventional method as comparison to FIG. 7.

To compare with FIG. 7, FIG. 8 shows an expanded image of inner face 30a of tubular body constructed in a conventional method from the same video file as that used in this embodiment. Same as in FIG. 7, in the diagram, the lateral direction corresponds to the inside diameter of the tubular body 30, and the vertical direction corresponds to the axial direction of the tubular body 30. It is known from FIGS. 7 and 8 that the change in luminance information acquired by the method of the embodiment nearly coincides with the change in luminance information acquired by the conventional method.

Figure 9A:
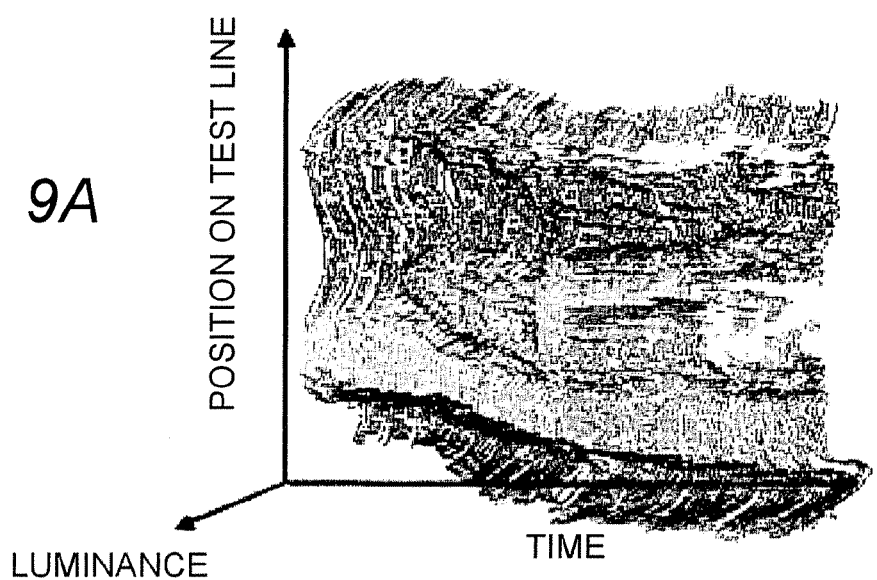
FIG. 9A is a three-dimensional graph showing distribution of luminance information for Red color of each pixel composing a three-dimensional image.
Figure 9B:
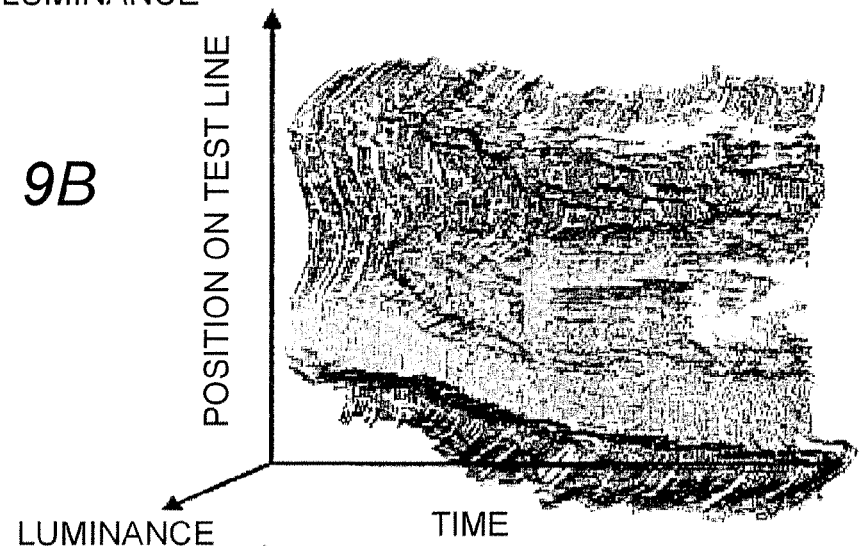
FIG. 9B is a three-dimensional graph showing distribution of luminance information for Green color of each pixel composing a three-dimensional image.
Figure 9C:
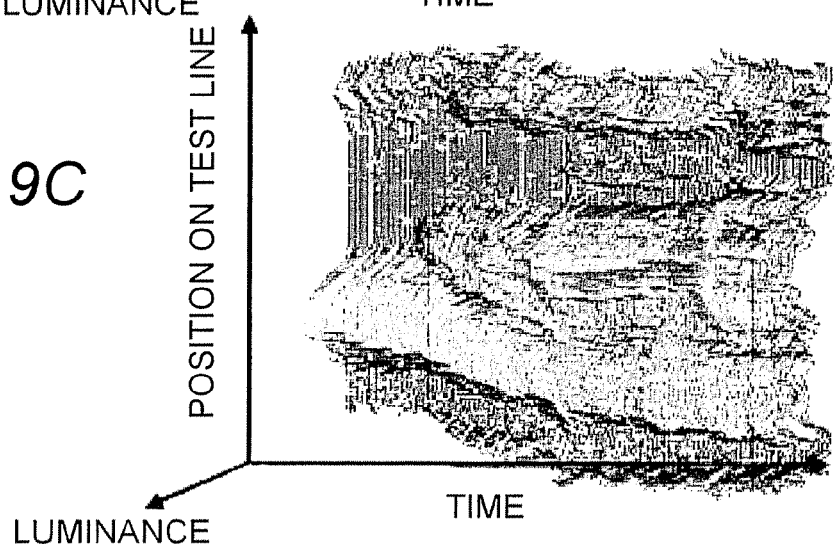
FIG. 9C is a three-dimensional graph showing distribution of luminance information for Blue color of each pixel composing a three-dimensional image.
Figure 10:
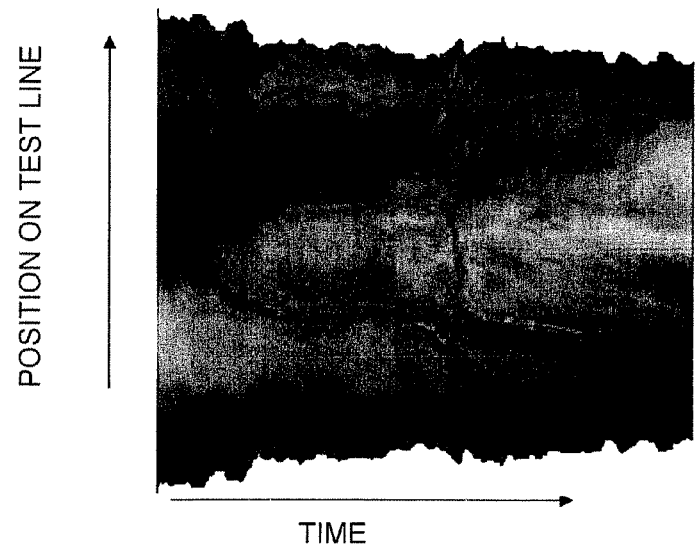
FIG. 10 is a diagram of expanded image of inside of tubular space as seen from the viewing point set in a direction perpendicular to a plane including the "time"-axis and "position on test line"-axis and at the positive side of the "luminance"-axis in FIGS. 9A, 9B and 9C.

FIGS. 9A, 9B, and 9C are three-dimensional graphs showing distribution of luminance information about red, green and blue of each of pixels composing the three-dimensional image of the inner face 30a of tubular body. In the three-dimensional graphs, aside from the axis showing "luminance," the axis showing the "time" corresponding to the axial direction of the tubular body 30, and the axis showing the "position on the test line" corresponding to the inside diameter of the tubular body 30 are provided. FIG. 10 shows expanded images as seen from the viewing point set in a direction perpendicular to the plane including the axes of "time" and "position on the test line" and at the positive side in the axial direction of luminance, corresponding to FIGS. 9A, 9B, and 9C.

Figure 11:
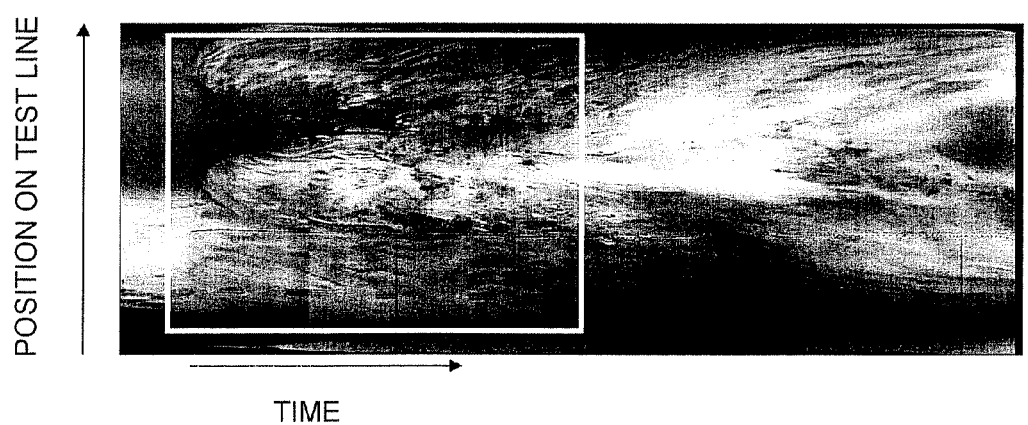
FIG. 11 is a diagram of expanded image of inside of tubular space formed in a conventional method, as comparison to FIG. 7.

To compare with FIG. 10, FIG. 11 shows an expanded image of inner face 30a of tubular body constructed by a conventional method from the same video file as that used in this embodiment. FIG. 11 corresponds to the expanded image in FIG. 8 which is rotated by 90 degrees in counterclockwise direction, and the region enclosed in a white frame in FIG. 11 is a region corresponding to the expanded image in FIG. 10. In FIG. 11, the directions indicating the "time" and the "position on inner cross section of tubular body" correspond to the direction of the axes showing the "time" and the "position on the test line", respectively, in FIGS. 9 and 10.

It is also known from FIG. 10 and FIG. 11 that the change in luminance information acquired by the method of this embodiment nearly coincides with the change in luminance information acquired by the conventional method.

According to the verification conducted by the applicant of the present application, when observing the inner face 30a of tubular body, the most excellent detection sensitivity was obtained when the luminance of green was used for constructing a three-dimensional image, and a three-dimensional image more similar to the actual shape of the observation was obtained. Successively, a favorable detection sensitivity was obtained in the sequence of blue and red. Basically, depending on the hue of the observation object, by selectively using the luminance information of green color or blue color or red color or mixed color thereof, a three-dimensional image of high fidelity to the actual observation object was obtained. For example, when the observation object is the digestive tract or tubular organ of a patient, by using the luminance information related to hue of wavelength similar to the complementary color of the hue of the observation object, for example, the luminance information related to green, a three-dimensional image of higher more similar to the actual observation object may be obtained.

More strictly, in the embodiment, when expanding and arraying the pixels, the position information is reflected in the depth direction calculated on the basis of the luminance information of pixels. Regarding the position information, for example as shown in FIG. 12, the position information in the depth direction is calculated from the luminance information of each pixel based on the relation of luminance and distance in which they relatively change exponentially. More specifically, as the luminance information is larger, the distance between the object lens 2a (see FIG. 4) and the observation object is shorter, and it is judged that the observation object projects, setting the position information in the depth direction to a large value. Thus, the convex and concave profile in the depth direction of the observation object can be recognized.

Figure 13A:
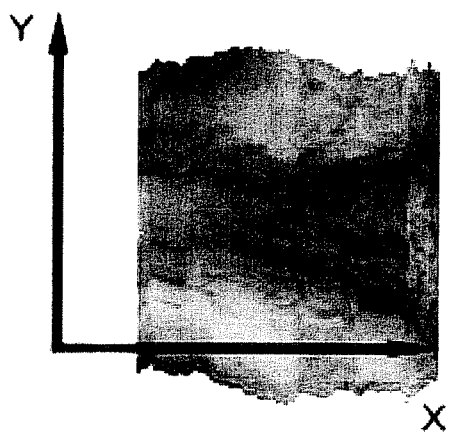
FIG. 13A is a diagram of three-dimensional image as seen from the viewing point set in a direction perpendicular to the X-Y plane and at the positive side in depth direction.

FIG. 13A shows a three-dimensional image as seen from the viewing point set in a direction perpendicular to the X-Y plane and at the positive side of the depth direction (Z-axis direction). Although not shown herein, the Z-axis extends so that the near side of the sheet of FIG. 13A is a positive direction along the depth direction.

Figure 13B:
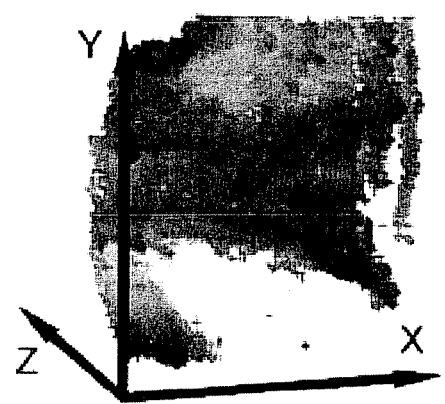
FIG. 13B is a diagram of three-dimensional image of the image in FIG. 13A being pulled up obliquely to left, and rotated about the Y-axis.
Figure 13C:
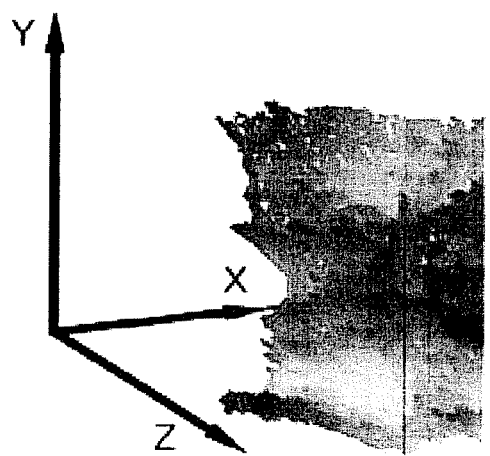
FIG. 13C is a diagram of three-dimensional image of the image in FIG. 13A being pulled down obliquely to right, and rotated about the Y-axis.

FIG. 13B shows a three-dimensional image obtained when the image shown in FIG. 13A is pulled up obliquely to left and rotated about the Y-axis. FIG. 13C shows a three-dimensional image obtained when the image shown in FIG. 13A is pulled down obliquely to right and rotated about the Y-axis.

The pixels composing the images shown in FIGS. 13A, 13B, and 13C may be added with RGB values preliminarily extracted. This allows a three-dimensional image more similar to the actual observation object to be constructed, and the feature of the inner face 30a of tubular body as the observation object may be obtained more easily.

Figure 14:
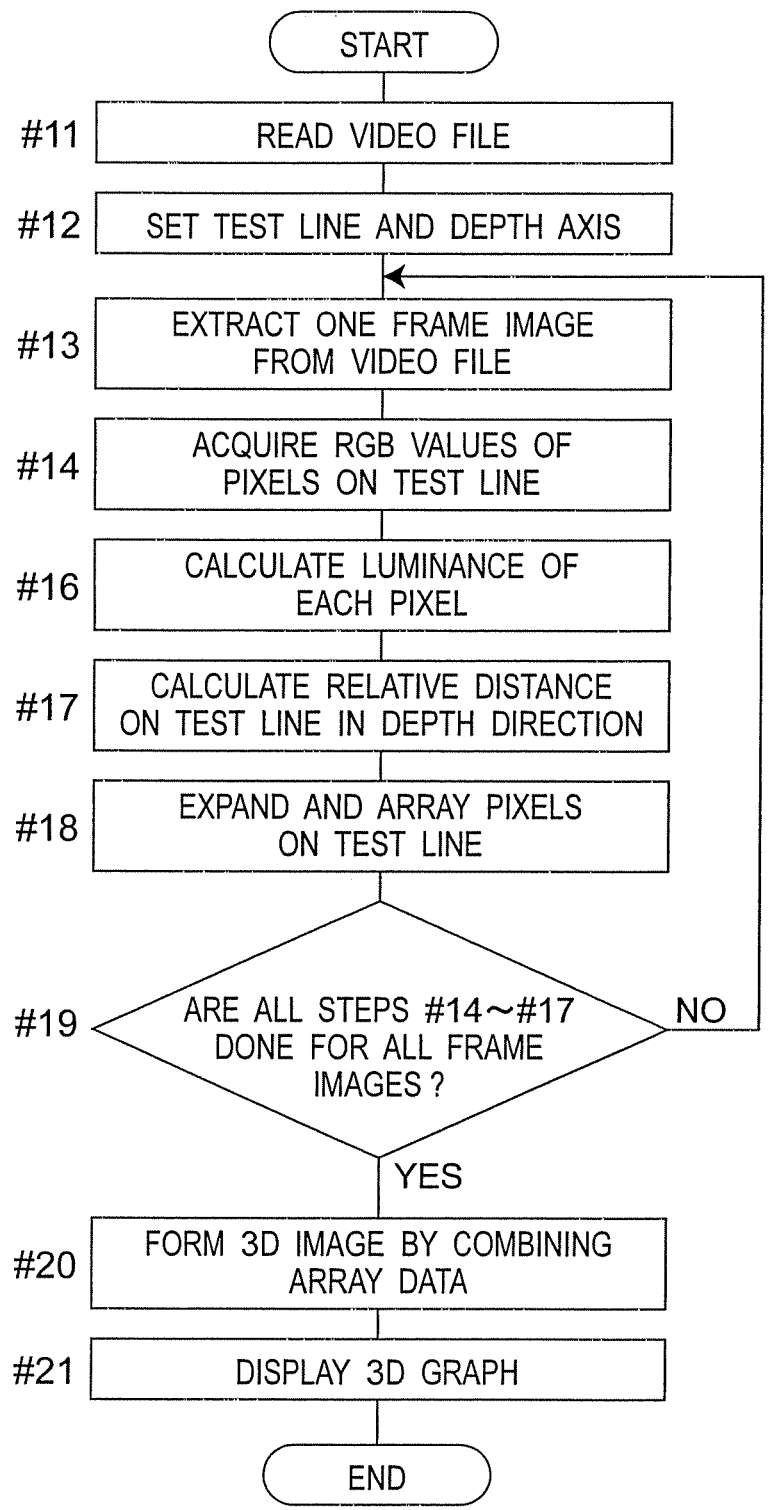
FIG. 14 is a flowchart of three-dimensional image forming process in Embodiment 1.

FIG. 14 is a flowchart of a three-dimensional image forming process to be executed according to a three-dimensional image forming program in the information processing device 20, that is, a process from inputting video file acquired at the endoscopic device 10 to the information processing device 20 until forming a three-dimensional image.

In this process, first, the video file acquired at the endoscopic device 10 is read (#11). Then the test line is set as shown in FIG. 5 (#12). The test line is applied commonly in all frame images extracted from the video file in the subsequent steps. Further at step #12, for construction of a three-dimensional image, the depth axis corresponding to the Z-axis explained with reference to FIG. 13 is determined to represent the position information of each pixel on the depth direction.

In succession, one frame image is extracted from the read video file (#13). Then RGB values are acquired as color information of each pixel located on the test line set at step #12 (#14).

On the basis of the RGB values acquired at step #14, the luminance of each pixel on the test line is calculated (#16). The information about the relative distance in the depth direction on the test line is acquired from the luminance, on the basis of the exponentially relatively changing relation of the distance and luminance shown in FIG. 12 (#17). Specifically, the relative distance from the objective lens of the endoscope 2 to each point on the test line and inside of the tubular structure is calculated. According to the invention, a three-dimensional image is formed on the basis of the relative distance between the objective lens of the endoscope and each point inside the tubular structure. Thus, when the relative distance information of pixel on the test line, that is, the position information is obtained, the pixels extracted from one frame image are arrayed with the position information reflected in the array (#18).

Further, it is judged whether the steps #14 to #18 are terminated on all frame images (#19). If not terminated on all frame images, the process returns to step #13 to repeat the subsequent steps to different frame images. When terminated on all frame images as judged at step #19, the arrayed pixels are combined to form a three-dimensional image (#20). Finally, the three-dimensional graph as shown in FIG. 9 is displayed (#21), and the process is terminated.

Although not particularly shown as a step, the three-dimensional image and three-dimensional graph at steps #20 and #21 may be stored in the hard disk 24 as required. This three-dimensional image forming process may be executed in parallel to the process of acquiring the video file at the endoscopic device 10. Alternatively, the video file acquired at the endoscopic device 10 may be once stored at the information processing device 20, and then executed as required. The three-dimensional image forming process is executed by reading out a three-dimensional image forming program stored in the ROM 22 or the hard disk 24 in the information processing device 20. This program may be pre-installed as part of programs based on which control is done by the CPU 11 of the information processing device 20. Alternatively, it may be additionally stored in the hard disk 24 of the information processing device 20 as three-dimensional image forming program which is carried in an external recoding medium such as CD-ROM, DVD-ROM, optical disk 18 or floppy disk 19 (see FIG. 1), or downloaded via network.

As clear from the description herein, according to the three-dimensional image forming device 1 of the embodiment, a three-dimensional image of irregular-shaped and moving inner face 30a of tubular body can be easily formed on the basis of the luminance information. Conventionally, multiple images must be taken in order to record an endoscopic image, but a three-dimensional image including the entire observation range can be formed. Thus the user can easily recognize the position and shape of the diseased portion, and can record objectively the information of the hardness and motion of tissues. As a result, the diagnostic precision of endoscopic examination is enhanced, and the memory capacity for storing the images can be reduced while the image reviewing time is shortened.

Embodiment 2

In this embodiment, the motion in the circumferential direction and axial direction of the endoscope 2 is detected to correct the expanded image according to the detected motion. As a result, it is possible to obtain an image reproducing more precisely the actual state of inner face of the tubular body. For this purpose, the three-dimensional image forming device of this embodiment further includes a motion detecting device for detecting the motion of the endoscope 2 in addition to the configuration of Embodiment 1.

FIG. 15 shows a configuration of the motion detecting device. The motion detecting device 50 includes an axial direction sensor 51 for detecting motion amount of the endoscope 2 in the axial direction of the endoscope 2, and a circumferential direction sensor 52 for detecting motion amount of the endoscope 2 in the circumferential direction of the endoscope 2. The sensors 51 and 52 are easily realized by using mechanism of a mouse generally used as a pointing device of a personal computer. The motion detecting device 50 detects the motion amount of the endoscope 2 from a reference position in the axial direction, and the motion amount of the endoscope 2 from a reference position in the circumferential direction to output detected data to the information processing device 20. The information processing device 20 receives the detected data from the motion detecting device 50, and relates time information showing the reception time (corresponding to the detection time), the motion amount in the axial direction, and the motion amount in the circumferential direction, and stores them as motion information of endoscope in a specified storage device such as hard disk 24. When disposing the expanded images (arrayed pixels), the information processing device 20 performs correction in the circumferential direction and the axial direction on the basis of the motion information. The time information showing the reception time (corresponding to the detection time) is not particularly specified. Any time information can be used, as far as it can provide relation between the imaging time of each image frame of video file and the detected values by the motion detecting device 50. For example, the JST (Japan Standard Time), GMT (Greenwich Mean Time), other standard time, or information showing the lapse of time from start of imaging of video images may be used.

Figure 16A:
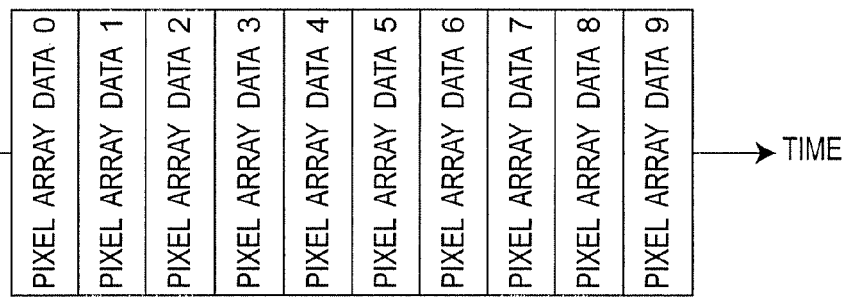
FIGS. 16A and 16B are diagrams for explaining correction of image in circumferential direction in Embodiment 2.
Figure 16B:
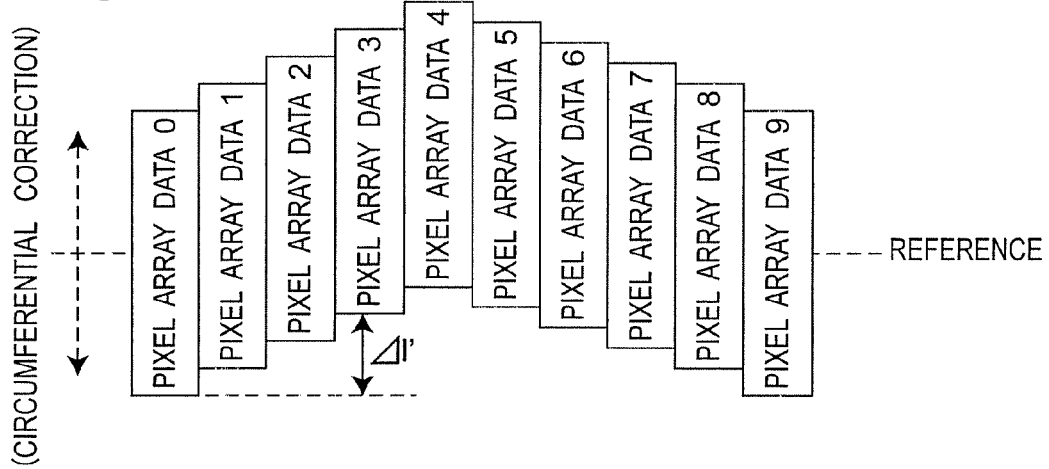

Referring now to FIG. 16, image correction in circumferential direction is explained. The circumferential direction sensor 52 of the motion detecting device 50 detects the change amount in the circumferential direction of the endoscope 2, that is, the rotation amount. When the change amount detected by the circumferential direction sensor 52 is $\Delta 1$, in the expanded image, as shown in FIG. 16B, the pixel data on the test line ("pixel array data") is shifted and disposed in the circumferential direction by the amount $\Delta 1'$ corresponding to the change amount $\Delta 1$. By thus correcting, distortion of image due to rotation of the endoscope 2 can be corrected.

Figure 17A:
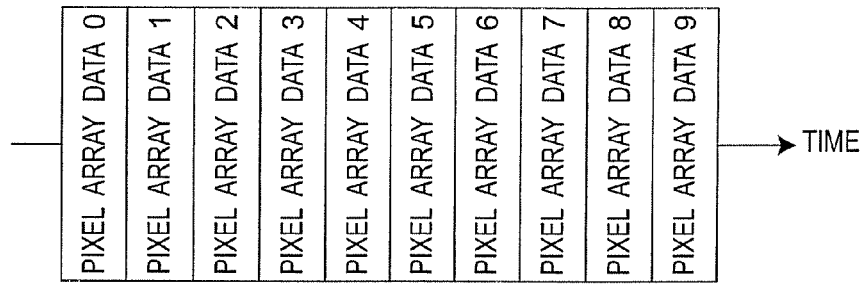
FIGS. 17A to 17C are diagrams for explaining correction of image in axial direction in Embodiment 2.

Referring next to FIG. 17, image correction in axial direction is explained. The axial direction sensor 51 of the motion detecting device 50 detects the change amount in the axial direction of the endoscope 2. In embodiment 1, as shown in FIG. 17A, the pixel array data obtained in time series from the video file was sequentially disposed to generate an expanded image. However, actually, the moving speed of the endoscope 2 is not always constant. That is, when the moving speed of the endoscope 2 is nearly zero, a plurality of images may be obtained at the same position on the inner face of the tubular body. When the moving speed of the endoscope 2 is faster, images at distant positions on the inner face of the tubular body may be obtained.

Figure 17B:
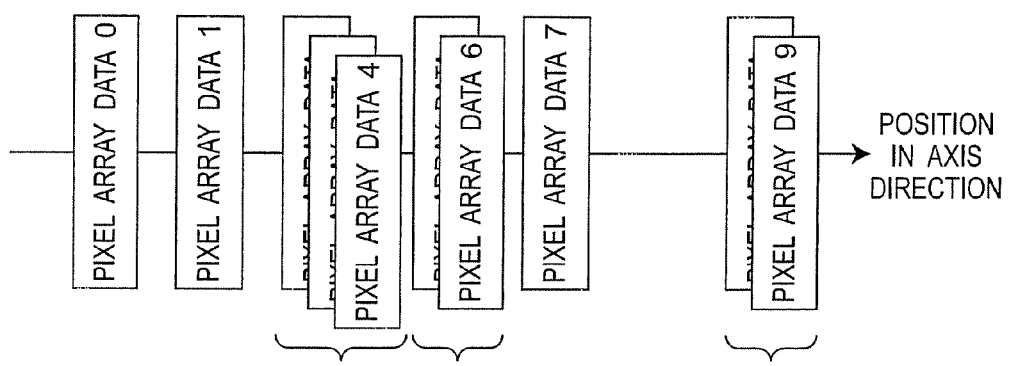

FIG. 17B is a diagram showing an example of pixel array data obtained in time series from the video file disposed on a position corresponding to the actual physical position. In the diagram, the positions (moving amounts) in the axial direction of pixel array data 2 to 4, pixel array data 5 to 6, and pixel array data 8 to 9 when acquiring those pixel array data are nearly the same. Thus the pixel array data 2 to 4, 5 to 6, and 8 to 9 are shown in overlaid state, respectively. This means that the moving speed of the endoscope 2 when acquiring these data is zero or very slow. On the other hand, regarding the adjacent pixel array data 0 and 1, or pixel array data 7 and 8, differences in the motion amount in the axial direction when acquiring these data are large, and hence pixel array data 0 and 1, or pixel array data 7 and 8 are disposed at distant positions, respectively. This means that the moving speed of the endoscope 2 when acquiring these data is very fast. In this case, it means that the image data is not acquired in a relatively long portion between the position corresponding to the pixel array data 0 (or 8) and the position corresponding to the pixel array data 1 (or 9) on inner face of tubular body.

Figure 17C:
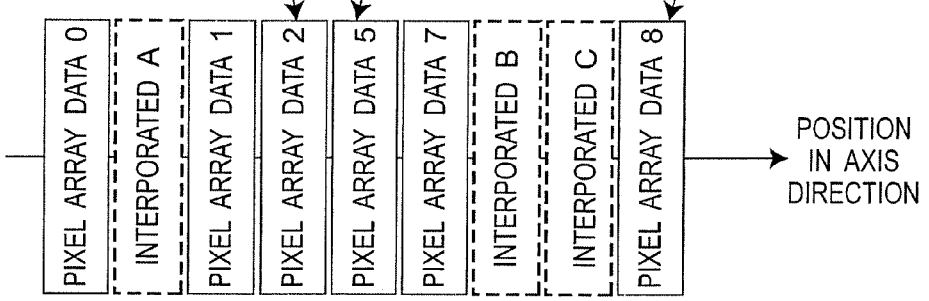

In the embodiment, as shown in FIG. 17C, it is designed to employ either one piece of data when there are a plurality of pieces of pixel array data showing images at nearly same positions in the inner face of tubular body, such as pixel array data 2 to 4, pixel array data 5 to 6, and pixel array data 8 to 9. On the other hand, when the interval is wide, for example, between pixel array data 0 and pixel array data 1, or pixel array data 7 and pixel array data 8, the intervening data is interpolated from the data at both ends. For example, as shown in FIG. 17C, interpolated data A is created from pixel array data 0 and pixel array data 1 and is disposed between pixel array data 0 and pixel array data 1. Preferably, the number of interpolation data to be disposed between pixel array data may be determined properly depending on the interval. For example, when the interval is large, such as the interval between pixel array data 7 and pixel array data 8, a plurality of pieces of interpolation data B and C are generated by linear interpolation and disposed. More specifically, the resolution (the number of pixel array data disposed per unit time) may be set in the axial direction (time direction) for the expanded image, and the pixel array data may be decimated or interpolated depending on the resolution.

Thus, correction of the images on the basis of the detected values in the axial direction and circumferential direction can reproduce an image much similar to the actual inner state of tubular body. In this way, since the reproductivity of inner state of tubular body can be improved, at the time of diagnosis, the hardness of biological tissues inside the tubular body and the motion of inner face of tubular body can be judged more accurately.

Figure 18A:
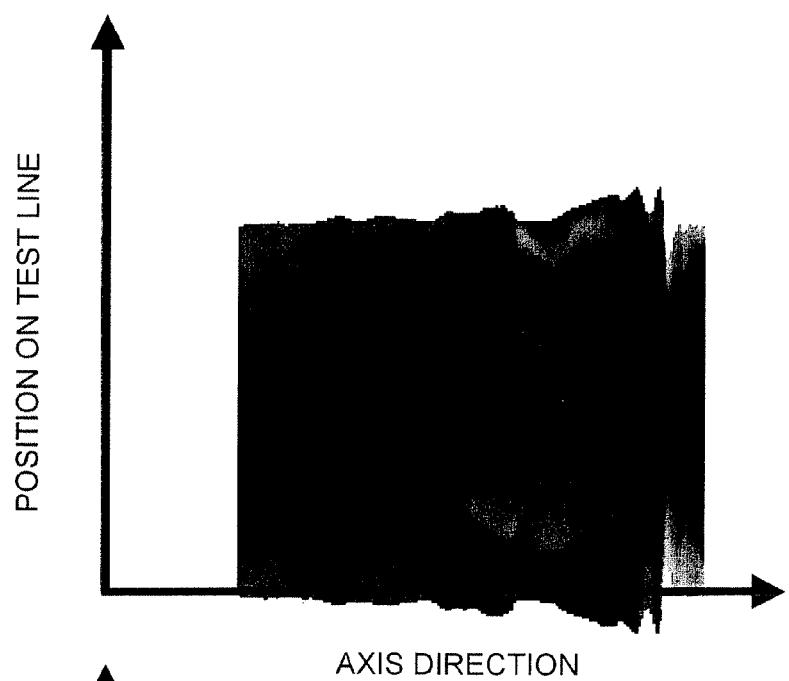
FIG. 18A is a diagram of expanded inside image of tubular part with no correction in circumferential and axial direction.
Figure 18B:
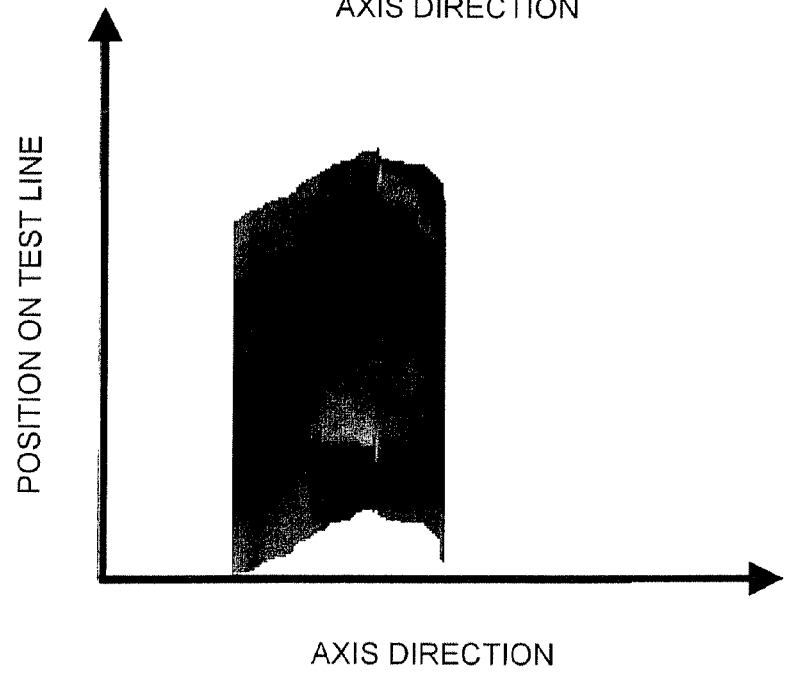
FIG. 18B is a diagram of expanded inside image of tubular part with correction in circumferential direction and axial direction.

FIG. 18A is a diagram of an image expanded and arrayed in the method of embodiment 1 without correction in the axial direction and circumferential direction. Applying the correction in the axial direction and circumferential direction in the embodiment to the image data shown in FIG. 18A provides a corrected image as shown in FIG. 18B.

Figure 19:
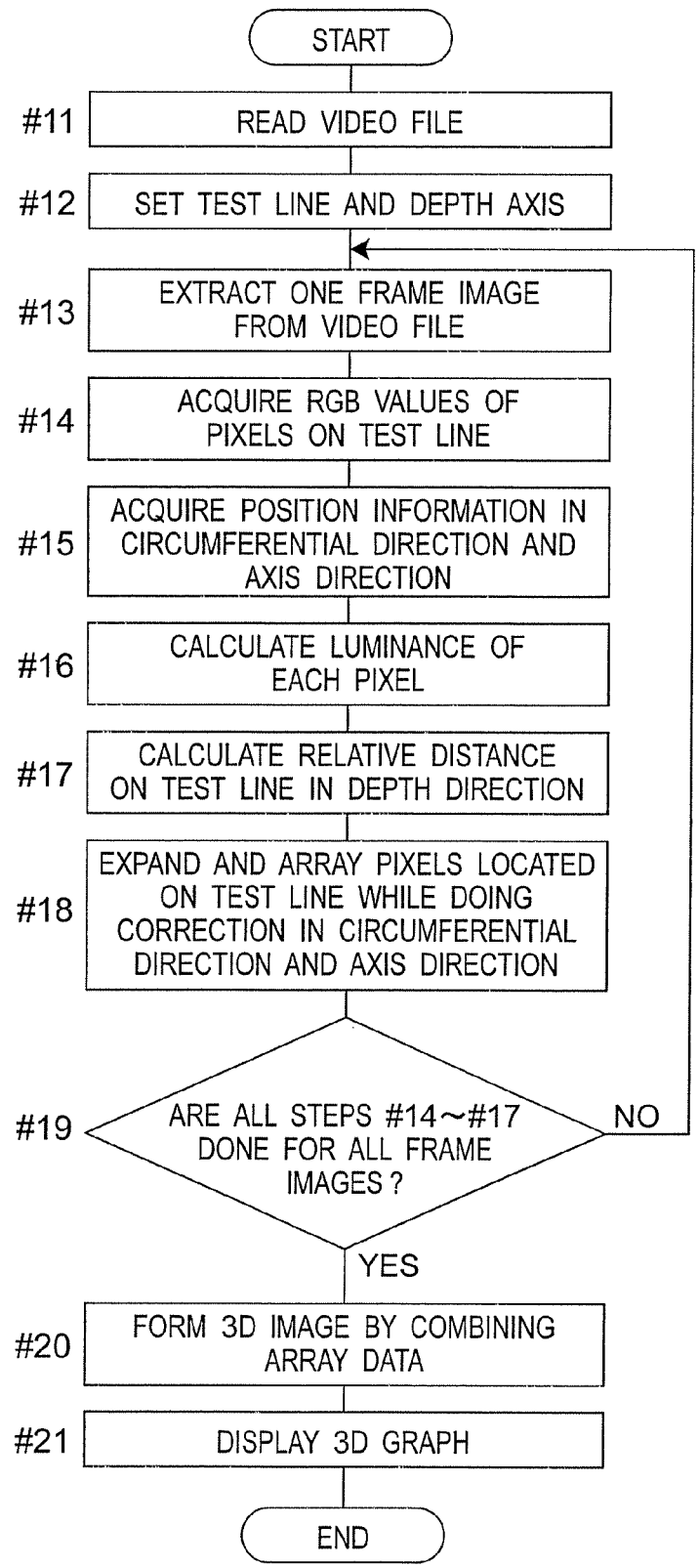
FIG. 19 is a flowchart of three-dimensional image constructing process in Embodiment 2.

FIG. 19 is a flowchart of process of executing the three-dimensional image constructing process with correction based on the motion of the endoscope 2. In this flow chart, the new step #15 is added to the flowchart shown in FIG. 14 of embodiment 1 and the process of step #18 is different from the flowchart of embodiment 1. At step #15, the information processing device 20 reads out the motion information acquired by the detecting device 50 and stored in the information processing device 20 to get the position information in the circumferential direction and axial direction. In the pixel expanding and arraying process at step #18, the pixel array data is arranged with the correction in the circumferential direction and axial direction applied to the arrangement as mentioned above. The processes at other steps are same as those of embodiment 1.

In the embodiment, both circumferential direction and axial direction are corrected, but at least either one direction may be corrected. In this case, an image similar to the actual inner state of tubular body may also be reconstructed.

The invention is explained herein by showing specific embodiments, but the concept of the invention is not limited to the illustrated embodiments alone, but may be changed and modified or changed in design within a scope not departing from the true spirit of the invention. For example, the tubular body 30 is observed in the embodiments, but the invention may be specifically applied to observation of upper digestive tracts such as stomach, duodenum, and esophagus, lower digestive tracts such as large intestine, and small intestine, or urethra, ureter, or other various tubular organs.

The invention claimed is:

1. A three-dimensional image forming device for forming a continuous three-dimensional image on a basis of images of an inner face of a tubular structure to be observed, comprising:

an imaging unit having an optical axis extending in an axial direction of the tubular structure, for obtaining a plurality of frame images while moving in the tubular structure under a specified lighting condition;

a luminance information extracting unit for extracting luminance information of pixels corresponding to a specified range of each frame image of the inner face of the tubular structure acquired by the imaging unit;

a distance information calculating unit for calculating relative distances in a depth direction between points on the inner face of the tubular structure and an objective lens from the luminance information extracted by the luminance information extracting unit according to an inverse proportional relationship between the relative distance and the luminance;

a three-dimensional image forming unit for forming a three-dimensional image of the inner face of the tubular structure by arraying the pixels on the specified range of each frame image of the inner face of the tubular structure while reflecting the relative distances to the arraying, and combining the arrayed pixels for a plurality of frame images; and a detecting unit for detecting change amount of the imaging unit in at least one of a circumferential direction or an axial direction, wherein the three-dimensional image forming unit corrects the image three-dimensional image formed by the arrayed pixels in at least one of the circumferential direction or the axial direction on a basis of the change amount detected by the detecting unit, and in order to correct the three-dimensional image formed by the arrayed pixels, the three-dimensional image forming unit shifts the pixels on the specified range of each frame image in the circumferential direction based on the change amount of the imaging unit in the circumferential direction, and in order to correct the three-dimensional image formed by the arrayed pixels, the three-dimensional image forming unit interpolates or deletes the pixels on the specified range of each frame image based on the change amount of the imaging unit in the axial direction.

2. The three-dimensional image forming device according to claim 1, further comprising:
a color information extracting unit for extracting color information of pixels composing each frame image of the inner face of the tubular structure obtained by the imaging unit, and
a color information adding unit for adding the color information extracted by the color information extracting unit to each pixel composing the three-dimensional image formed by the three-dimensional image forming unit.

3. The three-dimensional image forming device according to claim 1, wherein the luminance information is luminance information about red, green, blue, or a mixed color thereof.

4. The three-dimensional image forming device according to claim 1, wherein the imaging unit is an endoscope.

5. The three-dimensional image forming device according to claim 1, wherein the images of the inner face of the tubular structure to be observed is composed of a series of images or a video image of the inner face of the tubular structure.

6. A three-dimensional image forming device for forming a continuous three-dimensional image on a basis of images of an inner face of a tubular structure to be observed, comprising:
an imaging unit having an optical axis extending in an axial direction of the tubular structure, for obtaining a plurality of frame images while moving in the tubular structure under a specified lighting condition;
a luminance information extracting unit for extracting luminance information of pixels corresponding to a specified range of each frame image of the inner face of the tubular structure acquired by the imaging unit;
a distance information calculating unit for calculating relative distances in a depth direction between points on the inner face of the tubular structure and an objective lens from the luminance information extracted by the luminance information extracting unit according to an inverse proportional relationship between the relative distance and the luminance;
a three-dimensional image forming unit for forming a three-dimensional image of the inner face of the tubular structure by arraying pixels on a test line of each frame image of the inner face of the tubular structure while reflecting the relative distances to the arraying, and combining the arrayed pixels for a plurality of frame images, the test line being a line or row of pixels in a frame that are extracted; and
a test line setting unit for setting on each frame image the test line with a center corresponding to the optical axis of the imaging unit, the test line being set in a same specified position on each frame image,
wherein the luminance information extracting unit extracts luminance information of pixels located on the test line in each frame image.

7. The three-dimensional image forming device according to claim 6, further comprising:
a color information extracting unit for extracting color information of pixels composing each frame image of the inner face of the tubular structure obtained by the imaging unit, and
a color information adding unit for adding the color information extracted by the color information extracting unit to each pixel composing the three-dimensional image formed by the three-dimensional image forming unit.

8. The three-dimensional image forming device according to claim 6, wherein the luminance information is luminance information about red, green, blue, or a mixed color thereof.

9. The three-dimensional image forming device according to claim 6, wherein the imaging unit is an endoscope.

10. The three-dimensional image forming device according to claim 6, wherein the images of the inner face of the tubular structure to be observed is composed of a series of images or a video image of the inner face of the tubular structure.

11. A three-dimensional image forming method for forming a continuous three-dimensional image on a basis of images of an inner face of a tubular structure to be observed, comprising the steps of:
extracting luminance information of pixels corresponding to a specified range of each frame image of the inner face of the tubular structure, each frame image being acquired under a specified lighting condition by an imaging unit moving in the tubular structure, the imaging unit having an optical axis extending in an axial direction thereof;
calculating relative distances in a depth direction between points on the inner face of the tubular structure and an objective lens from the luminance information according to an inverse proportional relationship between the relative distance and the luminance;
forming a three-dimensional image of the inner face of the tubular structure by arraying the pixels on a test line of each frame image of the inner face of the tubular structure while reflecting the relative distances to the arraying, and combining the arrayed pixels for a plurality of frame images, the test line being a line or row of pixels in a frame that are extracted; and
setting on each frame image the test line with a center corresponding to the optical axis of the imaging unit, the test line being set in a same specified position on each frame image,
wherein the luminance information extracting step extracts luminance information of pixels located on the test line.

12. A three-dimensional image forming method for forming a continuous three-dimensional image on a basis of images of an inner face of a tubular structure to be observed, comprising the steps of:
extracting luminance information of pixels corresponding to a specified range of each frame image of the inner face of the tubular structure, each frame image being acquired under a specified lighting condition by an imaging unit moving in the tubular structure, the imaging unit having an optical axis extending in an axial direction thereof;
calculating relative distances in a depth direction between points on the inner face of the tubular structure and an objective lens from the luminance information according to an inverse proportional relationship between the relative distance and the luminance;
forming a three-dimensional image of the inner face of the tubular structure by arraying the pixels on the specified range of each frame image of the inner face of the tubular structure while reflecting the relative distances to the arraying, and combining the arrayed pixels for a plurality of frame images; and
detecting change amount of the imaging unit in at least one of a circumferential direction or an axial direction,
wherein in the three-dimensional image forming step, three-dimensional images of the inner face composed by the arrayed pixels are combined for a plurality of frame images depending on the change amount of the imaging unit in at least one of the circumferential direction or the axial direction, and in the three-dimensional image forming step, in order to correct the image in the circumferential direction, the pixels on the specified range of each frame image are shifted in the circumferential direction based on the change amount of the imaging unit in the circumferential direction, and in order to correct the image in the axial direction, the pixels on the specified range of each frame image is interpolated or deleted based on the change amount of the imaging unit in the axial direction.

13. A non-transitory recording medium storing a three-dimensional image forming program which can be installed to an information processing device, for forming a continuous three-dimensional image on a basis of images of an inner face of a tubular structure to be observed, the program making the information processing device execute the procedures of:

extracting luminance information of pixels corresponding to a specified range of each frame image of the inner face of the tubular structure, each frame image being acquired under a specified lighting condition by an imaging unit moving in the tubular structure, the imaging unit having an optical axis extending in an axial direction thereof;

calculating relative distances in a depth direction between points on the inner face of the tubular structure and an objective lens from the extracted luminance information according to an inverse proportional relationship between the relative distance and the luminance; and forming a three-dimensional image of the inner face of the tubular structure by arraying the pixels on a test line of each frame image of the inner face of the tubular structure while reflecting the relative distances to the arraying, and combining the arrayed pixels for a plurality of frame images, the test line being a line or row of pixels in a frame that are extracted; and setting on each frame image the test line with a center corresponding to the optical axis of the imaging unit, the test line being set in a same specified position on each frame image, wherein in the luminance information extracting procedure, luminance information of pixels located on the test line is extracted.

14. A non-transitory recording medium storing a three-dimensional image forming program which can be installed to an information processing device, for forming a continuous three-dimensional image on a basis of images of an inner face of a tubular structure to be observed, the program making the information processing device execute the procedures of:

extracting luminance information of pixels corresponding to a specified range of each frame image of the inner face of the tubular structure, each frame image being acquired under a specified lighting condition by an imaging unit moving in the tubular structure, the imaging unit having an optical axis extending in an axial direction thereof;

calculating relative distances in a depth direction between points on the inner face of the tubular structure and an objective lens from the extracted luminance information according to an inverse proportional relationship between the relative distance and the luminance; and forming a three-dimensional image of the inner face of the tubular structure by arraying the pixels on the specified range of each frame image of the inner face of the tubular structure while reflecting the relative distances to the arraying, and combining the arrayed pixels for a plurality of frame images; and detecting change amount of the imaging unit in at least one of a circumferential direction or an axial direction, wherein in the three-dimensional image forming step, images composed by the arrayed pixels are combined for a plurality of frame images depending on the change amount of the imaging unit in at least one of the circumferential direction or the axial direction, and in the three-dimensional image forming step, in order to correct the three-dimensional image of the inner face of the tubular structure in the circumferential direction, the pixels on the specified range of each frame image are shifted in the circumferential direction based on the change amount of the imaging unit in the circumferential direction, and in order to correct the three-dimensional image of the inner face of the tubular structure in the axial direction, the pixels on the specified range of each frame image is interpolated or deleted based on the change amount of the imaging unit in the axial direction.

* * * * *